US009675664B2

(12) United States Patent
Sharma et al.

(10) Patent No.: US 9,675,664 B2
(45) Date of Patent: Jun. 13, 2017

(54) COMPOSITIONS, FORMULATIONS AND METHODS OF TREATING PREECLAMPSIA-TYPE DISORDERS OF PREGNANCY

(71) Applicant: Women & Infants' Hospital of Rhode Island, Providence, RI (US)

(72) Inventors: Surendra Sharma, Warwick, RI (US); Satyan Kalkunte, Providence, RI (US); Udo Markert, Jena (DE)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 14/676,132

(22) Filed: Apr. 1, 2015

(65) Prior Publication Data
US 2015/0238567 A1 Aug. 27, 2015

Related U.S. Application Data

(63) Continuation of application No. 13/147,993, filed as application No. PCT/US2010/023320 on Feb. 5, 2010, now abandoned.

(60) Provisional application No. 61/207,026, filed on Feb. 6, 2009.

(51) Int. Cl.
| | | |
|---|---|---|
| *A61K 38/16* | (2006.01) | |
| *A61K 38/00* | (2006.01) | |
| *A61K 38/17* | (2006.01) | |
| *A61K 31/196* | (2006.01) | |
| *A61K 31/60* | (2006.01) | |
| *A61K 31/603* | (2006.01) | |
| *A61K 31/616* | (2006.01) | |
| *A61K 38/38* | (2006.01) | |
| *A61K 45/06* | (2006.01) | |
| *C07K 14/47* | (2006.01) | |
| *G01N 33/78* | (2006.01) | |

(52) U.S. Cl.
CPC ........ *A61K 38/1709* (2013.01); *A61K 31/196* (2013.01); *A61K 31/60* (2013.01); *A61K 31/603* (2013.01); *A61K 31/616* (2013.01); *A61K 38/38* (2013.01); *A61K 45/06* (2013.01); *C07K 14/47* (2013.01); *G01N 33/78* (2013.01)

(58) Field of Classification Search
None
See application file for complete search history.

(56) References Cited

U.S. PATENT DOCUMENTS

| | | | |
|---|---|---|---|
| 4,816,388 A | 3/1989 | Sipe et al. | |
| 6,258,540 B1 | 7/2001 | Lo et al. | |
| 6,319,498 B1 | 11/2001 | Findeis et al. | |
| 6,495,330 B1 | 12/2002 | Rademacher et al. | |
| 6,620,590 B2 | 9/2003 | Groome et al. | |
| 6,735,529 B1 | 5/2004 | Wald et al. | |
| 7,816,095 B2 * | 10/2010 | Kiernan | G01N 33/6893 422/400 |
| 8,288,110 B2 * | 10/2012 | Lopez | C07K 7/08 435/7.1 |
| 2002/0160394 A1 * | 10/2002 | Wu | C07K 14/76 435/6.13 |
| 2004/0038305 A1 | 2/2004 | Poston et al. | |
| 2005/0074746 A1 | 4/2005 | Mor et al. | |
| 2005/0255114 A1 | 11/2005 | Labat et al. | |
| 2006/0057644 A1 | 3/2006 | Kelly et al. | |
| 2006/0183175 A1 | 8/2006 | Buhimschi et al. | |
| 2007/0020766 A1 | 1/2007 | Owen-Smith | |
| 2007/0104707 A1 | 5/2007 | Karumanchi et al. | |
| 2007/0178530 A1 | 8/2007 | Poston et al. | |
| 2007/0185200 A1 | 8/2007 | Savvidou et al. | |
| 2008/0131907 A1 | 6/2008 | Wang et al. | |
| 2009/0191624 A1 | 7/2009 | Walker et al. | |

FOREIGN PATENT DOCUMENTS

| | | | | |
|---|---|---|---|---|
| EP | 1 914 552 | * | 4/2008 | ............. G01N 33/68 |
| WO | WO 2006071469 A2 | | 7/2006 | |
| WO | WO 2008046160 A1 | | 4/2008 | |
| WO | WO 2009099603 A1 | | 8/2009 | |

OTHER PUBLICATIONS

Sibai et al 2005. Lancet 365:785-799.*
Pipkin et al. 1996. Brit. J. Ob. and Gyn. 103:603-607.*
Sekijima et al. 2006. Amyloid: J. Prot Folding Disorders. 13:236-249.*
DiFederico et al., "Preeclampsia is associated with widespread apoptosis of placental Cytotrophoblasts within the uterine wall", Am J Pathol 155:293-301 (1999).
Genebacev et al., "Invasive cytotrophoblast apoptosis in preeclampsia", Hum Reprod 14 (suppl 2):59-66 (1999).
Balkundi et al., "Labor-associated changes in Fas ligand expression and function in human placenta", Pediatr Res 47:301-08 (2000).
Venkatesha et al., "Soluble endoglin contributes to the pathogenesis of preeclampsia", Nat Med 12(6):642-49 (2006).
Peracoli et al., "Tumor necrosis factor-alpha in gestation and puerperium of women with gestational hypertension and preeclampsia", Am J Reprod Immunol 57(3):177-85 (2007).
Jonsson et al., "Cytokine mapping of sera from women with preeclampsia and normal 0pregnancies", J Reprod Immunol 70(1-2):83-91 (2006).
Banerjee et al., "Placental expression of interferon-gamma (IFN-γ) and its receptor IFN-γ R2 fail to switch from early hypoxic to late normotensive development in preeclampsia", J Clin Endocrinol Metab 90(2):944-52 (2005).
Hendler et al., "The levels of leptin, adiponectin, and resistein in normal weight, overweight, and obese pregnant women with and without preeclampsia", Am J Obstet Gynecol 193(3 Pt2):979-83 (2005).

(Continued)

*Primary Examiner* — Shulamith H Shafer
(74) *Attorney, Agent, or Firm* — Polsinelli, PC

(57) ABSTRACT

This invention discloses a method of and composition for treating a PE-type disorder in a subject in need of such treatment comprising administering to the subject a pharmaceutical composition containing a therapeutically effective amount of a TTR polypeptide in admixture with a pharmaceutically acceptable vehicle.

23 Claims, 10 Drawing Sheets

(56) References Cited

OTHER PUBLICATIONS

Shah, D.M., "Role of the renin-angiotensin system in the pathogenesis of preeclampsia", Am J Physiol Renal Physiol 288(4):F614-25 (2005).
Salmon et al., "Antiphospholipid antibodies and pregnancy loss: A disorder of inflammation", J Reprod Immunol 2008, vol. 77, No. 1, pp. 51-56.
Girardi et al., "Heparin prevents antiphospholipid antibody-induced fetal loss by inhibiting complement activation", Nat Med 10(11):1222-26 (2004).
Duan et al., "Isolation, characterization, cDNA cloning and gene expression of an avian transthyretin", Eur J Biochem 200:679-87 (1991).
Buxbaum et al., "Transthyretin protects Alzheimer's mice form the behavioral and biochemical effects of Aβ toxicity", Proc Natl Aced Sci 105:2681-86 (2008).
Stein et al., "Neutralization of transthyretin reverses the neuroprotective effects of secreted amyloid precursor protein (APP) in APPSw mice resulting in tau phosphorylation and loss of hippocampal neurons: support for the amyloid hyopothesis", J Neurosci 24(35):7707-17 (2004).
Myers et al., "Use of proteomic patterns as a novel screening tool in pre-eclampsia, J Obstet Gynaecol. 24(8):873-4 (2008). Park et al., Identification of proteomic biomarkers of preeclampsia in amniotic fluid using SELDI-TOF mass spectrometry", Reprod Sci. 15(5):457-68 (2008).
Mita et al., 1984, "Cloning and sequence analysis of cDNA for human prealbumin," published in Biochem. Biophys. Res. Commun. 124 (2), 558-564.
Kanda et al., "The amino acid sequence of human plasma prealbumin," J. Biol. Chem. 249: 6796-6805.
Fex et al., "Interaction between prealbumin and retinol-binding protein studied by affinity chromatography, gel filtration and two-phase partition", Eur. J. Biochem. 1979, 99(2), 353-360.
Wilce et al., "Synthesis of an analog of the thyroid hormone-binding protein transthyretin via regioselective chemical ligation", J. Biol. Chem. 2001, vol. 276, No. 28, pp. 25997-26003.
International Search Report of PCT/US2010/023320 dated Apr. 13, 2010.

\* cited by examiner

RECOMBINANT TRANSTHYRETIN DOSE-DEPENDENTLY RESCUES SEVERE PE SERUM INDUCED DISRUPTED EC-HTR8 CROSSTALK IN TUBE ASSAY sPE: SEVERE PREECLAMPSIA (L1012, L13, L13, L2, L3 L17, L1020)

TRANSTHYRETIN RESCUES PREECLAMPSIA LIKE SYMPTOMS IN PREGNANT IL10 -/- MICE

FIG. 7
NEUTRALIZING ANTIBODY AGAINST TTR CONFER PE-LIKE FEATURES IN NPS: IN VIVO EVIDENCE

A

FETAL WEIGHT (g)

- NPS (n=22)
- NPS+IgY (n=24)
- NPS+TTR Ab (n=28) **

B

SYSTOLIC BLOOD PRESSURE (mmHg)

- NPS (n=3)
- NPS+IgY (n=3)
- NPS+TTR Ab (n=4) **

FIG. 8
NEUTRALIZING ANTIBODY AGAINST TTR CONFER PE-LIKE FEATURES IN NPS: IN VIVO EVIDENCE

PROTEINURIA (μg/mg)

FIG. 9
NEUTRALIZING ANTIBODY AGAINST TTR CONFER PE-LIKE FEATURES IN NPS: IN VIVO EVIDENCE

☐ YELLOW
▦ GREEN
▨ RED

NPS      NPS+TTR ANTIBODY (5 μg)

1
(10% v/v)

2

3

FIG. 9A
NEUTRALIZING ANTIBODY AGAINST TTR CONFER PE-LIKE FEATURES IN NPS: IN VIVO EVIDENCE

SEQUENCE LISTING

```
<160> NUMBER OF SEQ ID NOS: 3

<210> SEQ ID NO 1
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Pro Thr Gly Thr Gly Glu Ser Lys Ala Pro Leu Met Val Lys Val Leu
1               5                   10                  15

Asp Ala Val Arg Gly Ser Pro Ala Ile Asn Val Ala Val His Val Phe
            20                  25                  30

Arg Lys Ala Ala Asp Asp Thr Trp Glu Pro Phe Ala Ser Gly Lys Thr
        35                  40                  45

Ser Glu
    50

<210> SEQ ID NO 2
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Leu His Gly Leu Thr Thr Glu Glu Glu Phe Val Glu Gly Ile Tyr
1               5                   10                  15

Lys Val Glu Ile Asp Thr Lys Ser Tyr Trp Lys Ala Leu Gly Ile Ser
            20                  25                  30

Pro Phe His Glu His Ala Glu Val Val Phe Thr Ala Asn Asp
        35                  40                  45

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Arg Arg Tyr Thr Ile Ala Ala Leu Leu Ser Pro Tyr Ser Tyr Ser
1               5                   10                  15

Thr Thr Ala Val Val Thr Asn Pro Lys Glu
            20                  25
```

COMPOSITIONS, FORMULATIONS AND METHODS OF TREATING PREECLAMPSIA-TYPE DISORDERS OF PREGNANCY

CROSS REFERENCE TO RELATED APPLICATIONS

This application is a continuation of U.S. Ser. No. 13/147,993 filed Dec. 15, 2011 which is a national phase application of, and claims priority to, PCT/US2010/023320, filed on Feb. 5, 2010, which claims the benefit of priority under 35 U.S.C. §119(e) to U.S. Patent Application No. 61/207,026 filed on Feb. 6, 2009, the disclosures of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jun. 22, 2012, is named B19710US.txt and is 1,911 bytes in size.

BACKGROUND

Globally, preeclampsia (PE) and other hypertensive disorders of pregnancy are a leading cause of maternal and infant illness and death. By conservative estimates, these disorders are responsible for 76,000 maternal and 500,000 infant deaths each year, from 7-8% of all pregnancies. Typically, preeclampsia is diagnosed in the late 2nd or 3rd trimesters, after 20 weeks gestation, though its pathogenisis may occur earlier. Preeclampsia, HELLP Syndrome and eclampsia are manifestations of the same syndrome. Id. PE presents with maternal symptoms of global endothelial disease, including glomeruloendotheliosis, liver and cerebral vascularitis. It occurs only during pregnancy and the postpartum period and affects both the mother and the unborn baby. It is a rapidly progressive condition characterized by high blood pressure (>140) and the presence of proteinuria (>0.3 gm/ml) and general edema. Swelling, sudden weight gain, headaches and changes in vision can also be symptomatic. However, some women with rapidly advancing disease report few symptoms. It is believed to be a systemic disorder associated with a cascade of events and symptoms, including impaired trophoblast invasion, decreased placental perfusion, placental ischemia, oxidative stress and imbalance in angiogenic and prothrombotic factors which can lead to apoptosis of trophoblasts.[1-4] Studies have also reported that in preeclampsia, there are elevated levels of circulating or placental TNFα, IL-6, IL-8, IFNγ, leptin, a perturbed renin angiotensin system, complement split products, antibodies to phospholipids, sFlt-1, soluble endoglin, IL-12, decreased IL-10, NO, and hypoxia[5-13] amongst a host of other factors. Uteroplacental abnormalities can result in shallow placentation, poor spiral artery remodeling and placental ischemia. PE is believed to be a placental condition which resolves after pregnancy terminates/delivery.

Efforts have been made to provide assays for the diagnosis of PE. Numerous assays employ identification and/or measurement of various biochemical markers such as specific protein or nucleic acids in maternal samples.[14] Of these types of assays, noteworthy are those suggesting the use of transthyretin (hereinafter "TTR," formerly called prealbumin)) as a biomarker.[15]

In some instances of PE, labor is induced if the fetus has reached a gestational age of at least 37 weeks. If the pregnancy is premature, treatment focuses on allowing the fetus to mature as much as possible before inducing labor and avoiding progression of the disease and/or complications by close patient monitoring either by hospitalization or in an outpatient setting. The health of the mother is constantly weighed against the health of the fetus and labor induced when one or both are in danger of dying. In some cases, the fetus must be delivered immediately, regardless of gestational age, to save the mother's and/or fetus' lives.

A pharmaceutical composition for therapeutic intervention in PE and PE-type disorders would be a significant improvement in treatment.

SUMMARY OF THE INVENTION

We have discovered that administration of TTR to mammals exhibiting symptoms of preeclampsia alleviates the symptoms of this disorder.

The nucleotide sequence of TTR (identified by accession no. NM.sub.--000371) is disclosed in, e.g., Fex et al., 1979, "Interaction between prealbumin and retinol-binding protein studied by affinity chromatography, gel filtration and two-phase partition," published in Eur. J. Biochem. 99 (2), 353-360; Mita et al., 1984, "Cloning and sequence analysis of cDNA for human prealbumin," published in Biochem. Biophys. Res. Commun. 124 (2), 558-564, and the amino acid sequence of TTR (identified by accession nos. AAH05310, AAP35853) is disclosed in, e.g., Kanda et al., "The amino acid sequence of human plasma prealbumin," J. Biol. Chem. 249: 6796-6805, each of which is incorporated by reference herein in its entirety.

Because eclampsia and HELLP syndrome are manifestations of the same syndrome, administration of TTR should likewise treat and alleviate the symptoms of these disorders. Hereinafter, these three disorders collectively are referred to as PE-type disorders.

TTR is a known 55 kDa protein, a homotetramer with a dimer of dimers configuration (Uniprot:P02766). Each monomer is a 127-residue polypeptide rich in beta sheet structure. Association of two monomers forms an extended beta sandwich. Further association of another identical set of monomers produces the homotetrameric structure. The two thyroxine binding sites per tetramer sit at the interface between the latter set of dimers. Human and other mammalian TTR DNA sequences have been isolated [16-17], but to our knowledge TTR has not been employed as a pharmaceutical composition to treat PE-type disorders, or in a method for treating PE-type disorders. It has been suggested that increasing cerebral TTR synthesis is a potential therapeutic/prophylactic approach to human Alzheimer's disease[18], and the brains of mice have been treated in vitro with human TTR at a concentration of 3 μM[19]. It also has been suggested that formulations containing unspecified concentrations of TTR protein, fragments or mimics can be made and used to treat amyotrophic lateral sclerosis[20]. It is believed that the endogenous ligand for this protein is thyroxine T4.

Small molecules such as diclofenac or aspirin also are believed to stabilize the structure. In some embodiments small molecules including certain amino acids like tryptophan analogs or anti-oxidants and that are pregnancy compatible would improve pregnancy complications and provide unique new therapeutic opportunity to preeclampsia market. It is believed that such small molecules may fit into the ligand binding site. Again, without being bound by any particular theory, it is believed that the presence of ligands can stabilize the protein structures and can prevent misfoldings and aggregation of TTR protein.

In particular embodiments of this invention it is contemplated that the TTR, subunits or fragments thereof, or non-pathogenic TTR mutants (collectively "TTR polypeptide") are useful used in a pharmaceutical preparations or formulations to treat the PE-type disorders. In some instances subunits or non-pathogenic TTR mutants are established by stabilization of TTR tetrameric native structure, purified to homogeneity from cell sources or produced recombinantly or synthetically.

Accordingly, in one aspect, the invention comprises a method of treating a PE-type disorder in a mammal, preferably human, subject comprising administering to the patient a pharmaceutical formulation of a composition containing a therapeutically effective amount of a TTR polypeptide. By "therapeutically effective amount" is meant an amount of TTR polypeptide (alone or in combination with other drugs) that is effective in rescuing (i.e., preventing or arresting) abnormal endothelial-trophoblast cross-talk that is a hallmark of PE-type disorders. As to cross-talk, normal pregnancy serum will exhibit tube-vacuole formation of over about 40 tubes/well of a 48 well plate (for example between about 45 and 75 tubes/well. This average number of such tubes-vacuoles in response to normal pregnancy serum is defined as "normal endothelial-trophoblast cross-talk". In contrast, serum or plasma from a pregnant female at risk for or having preeclampsia will exhibit tube-vacuole formation substantially less than about 40 tubes per well (for example between about 5 and 35 tubes/well). This average number of such tubes-vacuoles is defined as "abnormal endothelial-trophoblast crosstalk". See Example 2 infra, U.S. Patent Application Ser. No. 61/063,491 filed Feb. 4, 2008 and Kalkunte et al., In Vitro and In Vivo Evidence for Lack of Vascular Remodeling by Third Trimester Trophoblasts, Placenta 29: 871-78 (2008) (PCT Patent Application No. PCT/US2009/000708). The PE-type disorder may be preeclampsia, Eclampsia or HELLP syndrome. The therapeutically effective amount of TTR polypeptide may comprise a TTR tetramer or a TTR subunit, active fragments thereof, or modified version thereof in admixture with a pharmaceutically acceptable vehicle.

In another aspect, the invention comprises PE-type disorder rescuing therapeutic compositions of TTR polypeptides. Such compositions comprise a therapeutically effective amount of a TTR polypeptide in admixture with a pharmaceutically acceptable vehicle. Such compositions can be systemically administered parenterally, intravenously or subcutaneously. When systemically administered, the pharmaceutical formulation for systemic administration is in the form of a pyrogen-free, parenterally acceptable aqueous solution. The preparation of pharmaceutically acceptable protein solutions or formulations, having due regard to pH, isotonicity, stability and the like, is within the skill in the art.

The invention also comprises preparations of a TTR polypeptide suitable for oral delivery. Suitable oral formulations may be prepared as an aqueous-based oral solution, or may comprise TTR polypeptide in the form of a gel, a suspension, a lozenge, a pill, a capsule or a coated or uncoated tablet.

In another aspect, the TTR polypeptides may be administered in compositions and formulations with one or more non-steroidal anti-inflammatory compositions ("NSAIDs"). Without being bound by any particular theory it is believed that NSAIDs exert their effect through binding to T4 binding pockets in TTR. Exemplary non-steroidal anti-inflammatory compositions include diclofenac, flufenamic acid, diflunisal and aspirin.

The dosage regimen involved in the method of treating PE-type conditions will be determined by the attending physician considering various factors that modify the action of drugs, for example the conditions, body weight, and diet of the patient, the severity of conditions, time of administration and other clinical factors. Generally, the daily regimen should be in the range of 50-500 micrograms of polypeptide per kilogram of body weight. Particular reference is made to dosages of 50-100 mg/kg, 25-50 mg/kg, and 20 mg/kg of recombinant or isolated human transthyretin protein over a 24 hour period. Further reference made to dosages of 10 mg/kg per day administered over a 24 hour period in combination with an NSAID such as diclofenac (10:1 mole/mole).

Since the half life of endogenous TTR is approximately 2 days, the treatment regimen can be titrated by measuring the serum levels of TTR by ELISA, and the dose adjusted accordingly by the attending physician. As the therapeutic method may also include co-administration with other compounds, in such cases, the dosage recited above would be adjusted to compensate for such additional components in the therapeutic composition.

The instant invention comprises a method of treating a PE-type disorder (e.g. preeclampsia, eclampsia and HELLP syndrome) in a subject in need of such treatment comprising administering to the subject a pharmaceutical composition containing a therapeutically effective amount of a TTR polypeptide in admixture with a pharmaceutically acceptable vehicle. In some embodiments of the method TTR polypeptide comprises TTR,

```
                                            (SEQ ID NO: 1)
H-PTGTGESKAPLMVKVLDAVRGSPAINVAVHVFRKAADDTW

EPFASGKTSE
                                            (SEQ ID NO: 2)
-NH-CH2-CH2-S-CH2-CO-ELHGLTTEEEFVEGIYKVEID

TKSYWKALGISPFHEHAEVVFTAND
                                            (SEQ ID NO: 3)
-NH-CH2-CH2-S-CH2-CO-PRRYTIAALLSPYSYSTTAVVT

NPKE-OH,
and
                                            (SEQ ID NO: 2)
Cl-Ac-ELHGLTTEEEFVEGIYKVEIDTKSYWK[[-]]ALGI SPFHEHAEVVFTAND
                                            (SEQ ID NO: 3)
-NH-CH2-CH2-S-CH2-CO-PRRYTIAALLSPYSYSTTAVV

TNPKE-OH.
```

In particular embodiments the therapeutically effective amount of TTR polypeptide is between about 50 and 500 micrograms per kilogram body weight and optionally about 50-100 mg/kg, with particular reference to 25-50 mg/kg. Further contemplated is administration over a 24 hour period as well as co-administration with a non-steroidal anti-inflammatory (NSAID).

In some embodiments TTR polypeptide is co-administered with NSAID at a molar ratio of TTR polypeptide to NSAID of from about 10:1 to about 1:1. Noted is co-administration wherein the non-steroidal anti-inflammatory composition is selected from the group consisting of diclofenac, flufenamic acid, diflunisal and aspirin. Specific embodiments of the method include co-administration of a TTR polypeptide and NSAID comprises within a dosage range of from about 5 to about 100 mg/kg/day. Noted in the employment of such method is the additional step of monitoring the level of serum transthyretin in said subject subsequent to said administration. Further noted is the method of employing the present composition therapeutically in treatment of kidney pathology, glomerular endotheliosis and excess excretion of protein or proteinuric disorders.

The invention yet further includes a therapeutic composition comprising a therapeutically effective amount of a TTR polypeptide in a pharmaceutically acceptable vehicle, optionally in the form of a pyrogen-free, parenterally acceptable aqueous solution for systemic administration. Noted as to such composition is TTR polypeptide in an amount of about 3.5 to about 500 mg. Additionally noted is TTR polypeptide is selected from the group consisting of recombinant TTR, mutants of TTR, synthetic TTR, pharmaceutically active fragments of TTR.

DESCRIPTION OF THE DRAWINGS

FIG. 2 Panels A, B and C illustrate that recombinant TTR dose dependently rescues severe PE serum induced disrupted EC-HTR8 crosstalk. FIG. 2 Panel A shows tubal assay results for normal serum (NPS).

FIG. 2 Panel B shows tubal assay results for severe preeclampsia serum (sPE).

FIG. 2 Panel C shows tubal assay results for sPE.

The data show serum from severe preeclampsia patients (sPE) (Panel B and C, photographs #5 & 9) but not normal pregnancy (NPS) (Panel A, photograph #1) inhibits the interaction between crosstalk of cellular partners' viz., endothelial cells (EC) and trophoblasts (HTR). Recombinant TTR in dose dependent manner rescues sPE serum induced disruption (Panels B and C, photographs #6-8 & 10-12). Please note representative photographs of sPE samples from two different patients are shown in Panel B & C.

Figure 3:
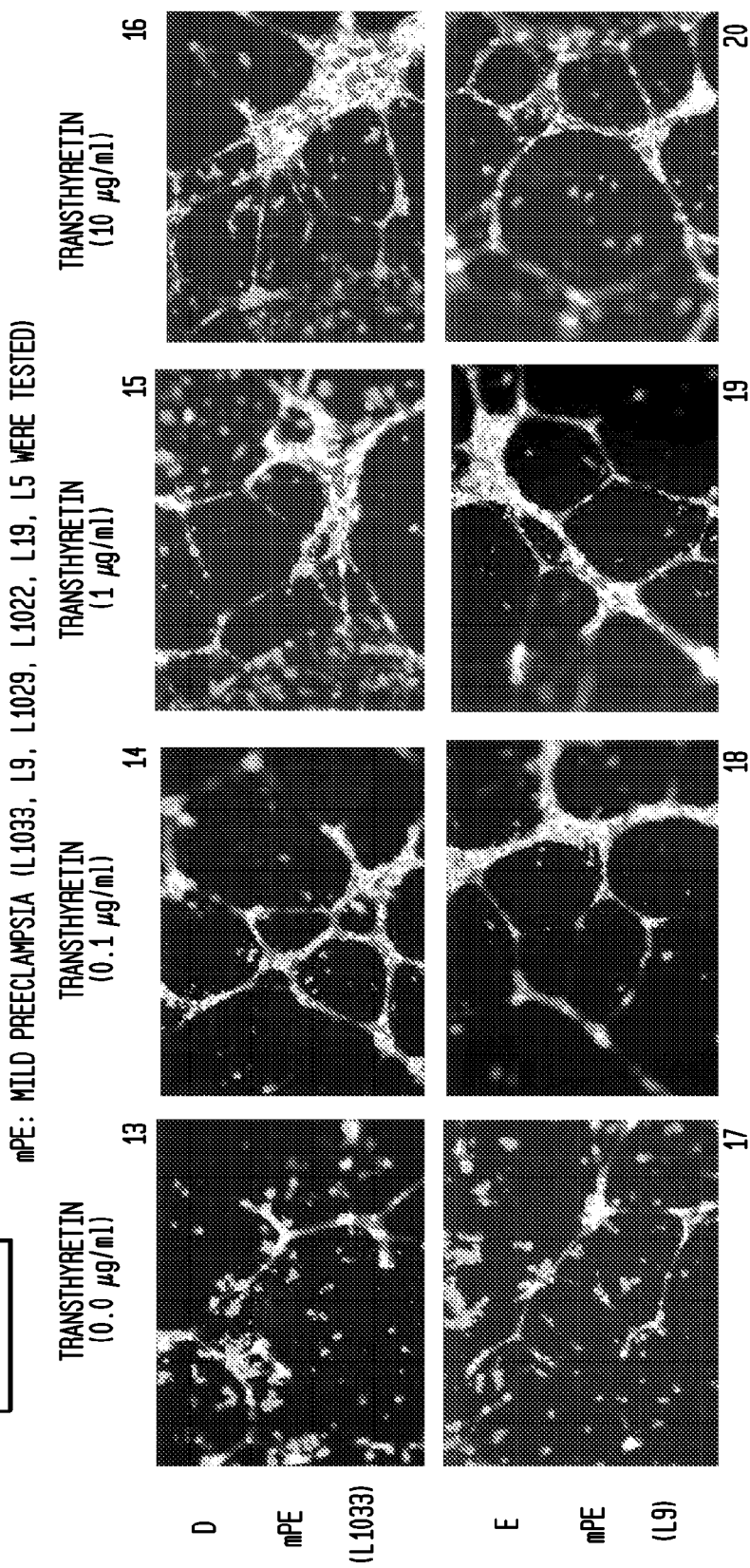

FIG. 3 presents data on recombinant transthyretin dose-dependent rescue.

FIG. 3 Panel D shows tubal assay results with mild PE (mPE) serum induced disrupted EC-HTR8 crosstalk in tube assay.

FIG. 3 Panel E shows tubal assay results with mPE. Tested were L1033, L9, L1029, L1022, L19, L5.

FIG. 3 Panel D and E illustrate that recombinant TTR dose dependently rescues mild PE serum induced disrupted EC-HTR8 crosstalk. NPS stands for normal serum and mPE for mild preeclampsia serum. The data show serum from mild preeclampsia patients (mPE) (Panel D and E, #13 & 17) inhibits the interaction between crosstalk cellular partners viz., endothelial cells (EC) and trophoblasts (HTR). Recombinant TTR in dose dependent manner rescues mPE serum induced disruption (Panels D and E, #14-16 & 18-20). Please note representative photographs of mPE samples from two different patients are shown in Panel D & E.

Figure 4:
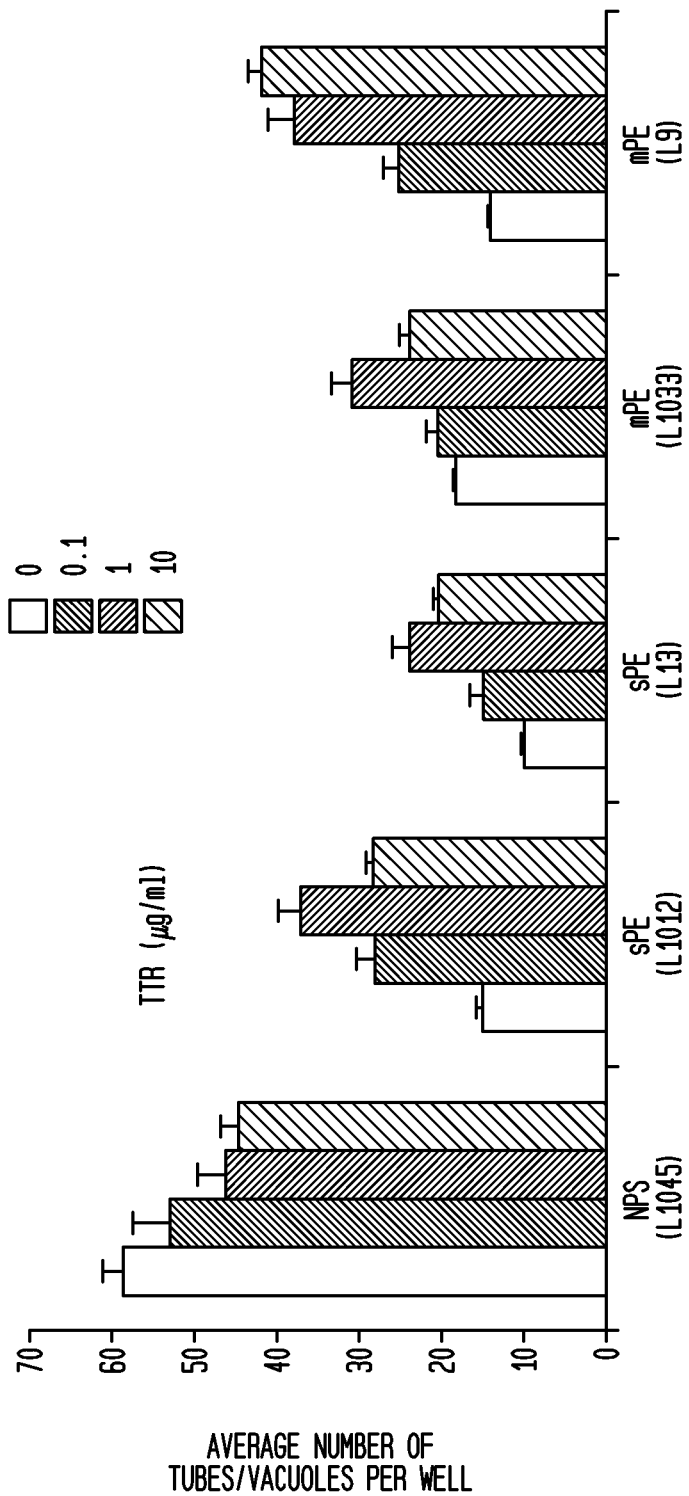

FIG. 4 is a graphic reproduction of the quantification of in vitro cross-talk and rescue results as described in Example 2.

Figure 5:
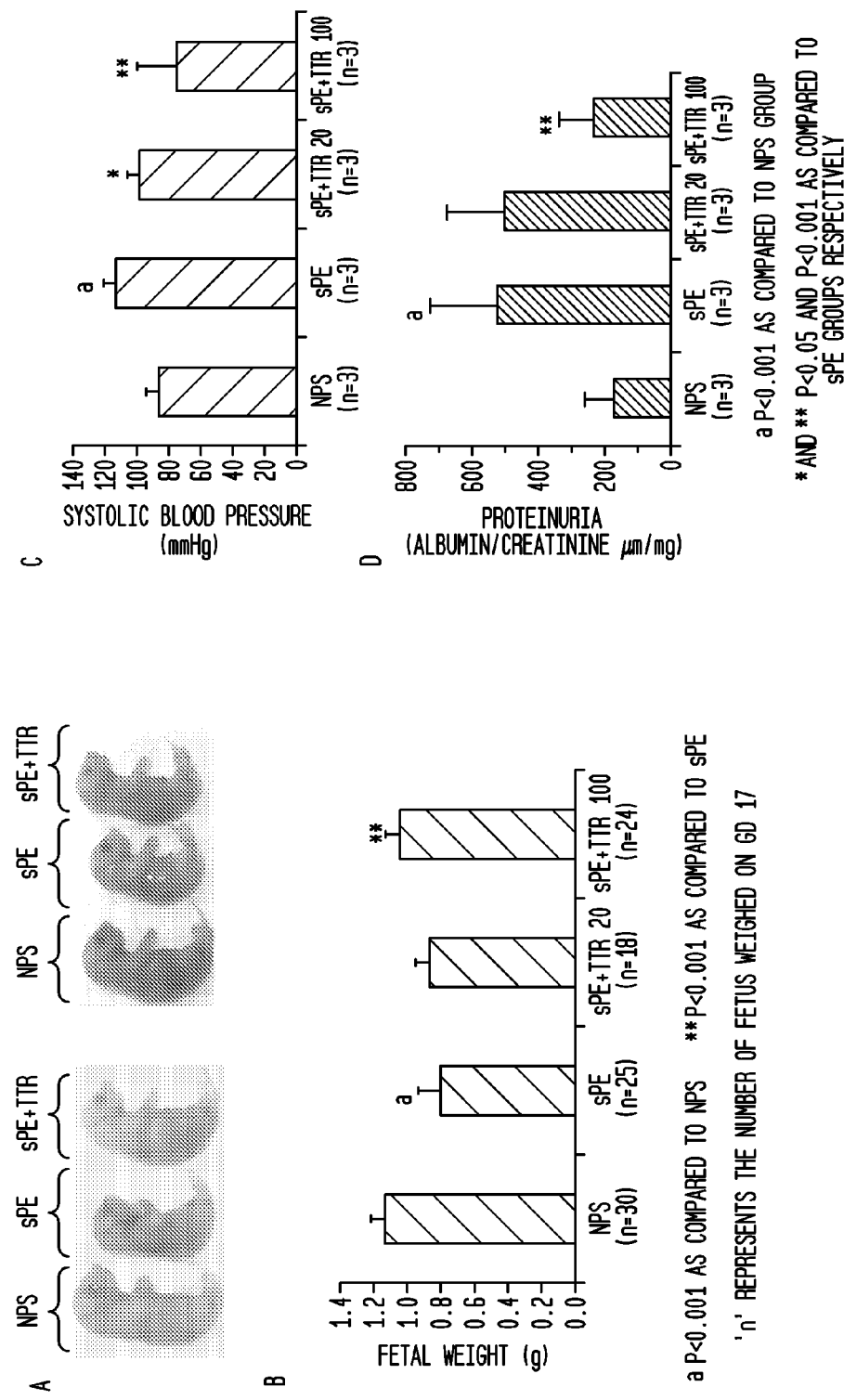

FIG. 5 shows the in vivo confirmation of the rescue of pregnancy by recombinant TTR. Briefly, a single intraperitoneal injection of 100 μl of serum from preeclampsia patients (sPE) but not normal pregnancy (NPS) in pregnant IL10 knockout mice induced intra-uterine growth restriction as shown by the fetal size in picture (A) and in the fetal weight graph (B), hypertension as seen by systolic blood pressure (C) and proteinuria (D). Importantly, co-administration of recombinant TTR rescues sPE serum induced anomalies (A-D) at different doses.

Figure 6:
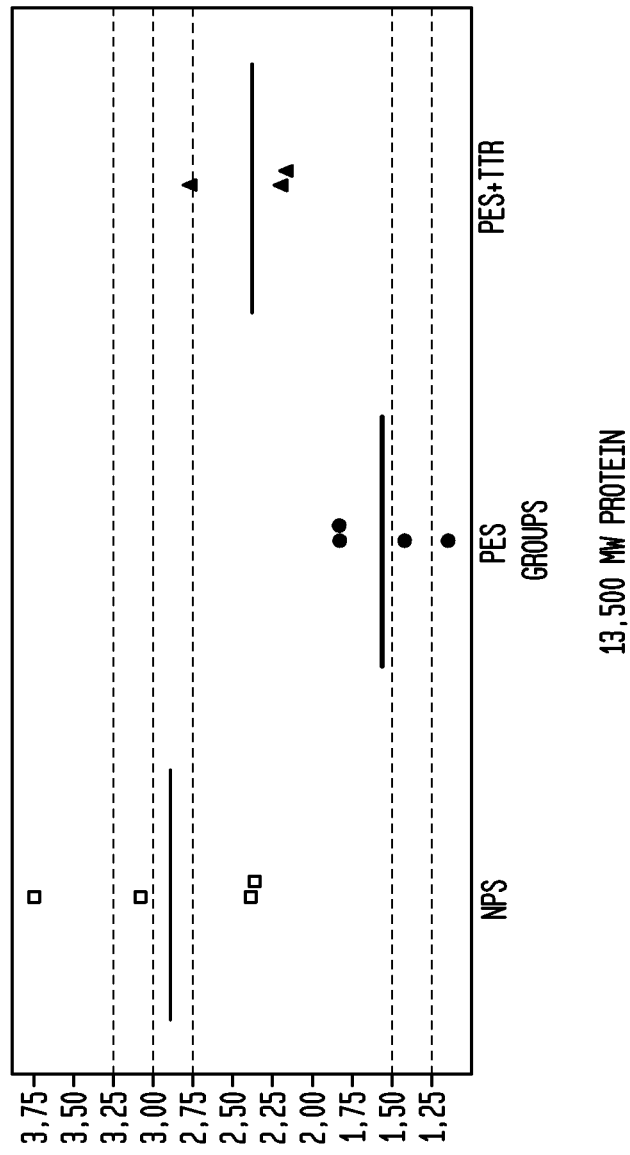

FIG. 6 shows the SEDI-TOF data of serum samples obtained from mouse from different treatment groups. As shown here, severe preeclampsia serum induces reduction of TTR levels in mouse which is then rescued by recombinant TTR administration as indicated by rising levels of TTR expressed as relative intensities.

FIG. 7 presents in vivo experimental data to confirm that when TTR activity is abolished using a neutralizing antibody, normal pregnancy serum (NPS) behaves like preeclampsia serum in that it causes intrauterine growth restriction as represented by the fetal weight graph (A) and cause hypertension as represented by the increase in systolic blood pressure seen in graph (B). Isotype control antibody (IgY) is used to show the specificity of the TTR neutralizing antibody. Note that ** indicates statistical significance at probability of greater than 95% confidence levels as compared to NPS group (expressed as $P<0.05$).

FIG. 8 presents in vivo experimental data to confirm that when TTR activity is abolished using a neutralizing antibody, normal pregnancy serum (NPS) behaves like preeclampsia serum in that it causes proteinuria. Isotype control antibody is used to show the specificity of the TTR neutralizing antibody. These findings further confirm that reduced TTR levels in serum can cause preeclampsia like symptoms and use of recombinant TTR can rescue the symptoms.

FIG. 9 data is based on an in vitro experiment. With neutralized TTR using a neutralizing antibody, normal pregnancy serum (NPS) behaves like preeclampsia serum in that it inhibits the interaction of endothelial cells and trophoblasts as seen in NPS+TTR antibody panels. These values have been quantified and shown graphically in FIG. 9a

DETAILED DESCRIPTION

Example 1

Proteomic Analysis of Normal Versus PE Serum

The early detection of biomarkers associated with preeclampsia would significantly decrease morbidity and mortality from this pregnancy complication but such early detection is difficult in the absence of physical symptoms, which tend to present later in pregnancy. Results clearly indicate that preeclampsia serum is different from normal pregnancy serum in its pathology-inducing properties. A mass spectrometry SELDI-TOF proteomics approach was used to determine which protein molecules are dysregulated (i.e., by loss of quantity and/or function or by overwhelming presence).

In order to detect low concentration proteins in a sample replete with highly abundant proteins, a separation of the low and high concentration proteins is useful. To accomplish this, different fractionation techniques based on diverse loading platforms can be employed. For example, protein binding to hydrophobic beads and their gradual elution may be employed. Alternatively, anion exchangers after pH value-dependent elution can be used.[21] Serum from normal and PE human patients was used for initial optimization of the experimental settings. The serum was analyzed in native form and analyzed after fractionation in one single procedure using 4 different coated protein chips: an anionic exchanging surface chip (Q10), a cationic exchanging surface chip (CM10), a hydrophobic surface chip (H50) and a copper (II) ion coated surface chip (IMAC30). For data generation, the IMAC30 chip was the one which allowed detection of the highest number of differentially expressed proteins.

First, the protein chips were activated in accordance with the manufacturer's protocol. The IMAC30 protein chips were loaded with 50 µl of IMAC charging 100 mM $CuSO_4$ solution and incubated for 10 minutes followed by washing with deionized water with 2 minutes incubation, repeated twice. This was followed by incubation with IMAC-neutralizing buffer (100 mM sodium acetate pH 4.0) repeated twice, then incubation with IMAC-binding buffer (100 mM sodium phosphate, 0.5 M sodium chloride, pH 7.0) for 5 minutes. Thereafter, the normal and PE serum samples were applied to the chips and incubated for 30 minutes in a humid chamber at room temperature. Room temperature will be understood to mean about 20° C. to about 25° C. Each application spot was then washed three times with binding buffer to avoid non-specific binding, followed by 2 washings with deionized water to remove salts. After air drying, 1 µl of sinapinic acid (SPA) dissolved in 50% acetonitrile and 0.05% trifluoroacetic acid (TFA) was applied twice to every spot. The spots were dried between the applications.

The cationic exchange protein chip CM10 was first rehydrated by incubation with CM-low-stringency binding buffer (100 mM sodium acetate, pH 4.0) or CM-high-stringency binding buffer (50 mM HEPES, pH 7.0) for 5 minutes and this rehydration step was then repeated once. Thereafter, the normal and PE serum samples were applied to the chips and incubated for 30 minutes in a humid chamber at room temperature. Afterwards, the spots were washed 3 times with binding buffer for 5 minutes and twice with deionized water. After air drying, SPA was applied on the spots as described above.

SELDI-TOF measurements were then performed on all of the chips using the ProteinChip System, Series 4000 SELDI-TOF mass spectrometer (Ciphergen Biosystems). Calibration was performed externally using the protein MW standard kit (Ciphergen Biosystems). Ionization of the proteins was affected with a laser shot energy of 2200 nJ in the case of proteins<20 kDa (low mass range) and 3500 nJ for proteins>20 kDa (high mass range). The final spectra of a spot was generated by combining the spectra of 320 laser shots. The bioinformatical analysis was performed using Ciphergen Express Client 3.0 software.

Figure 1:
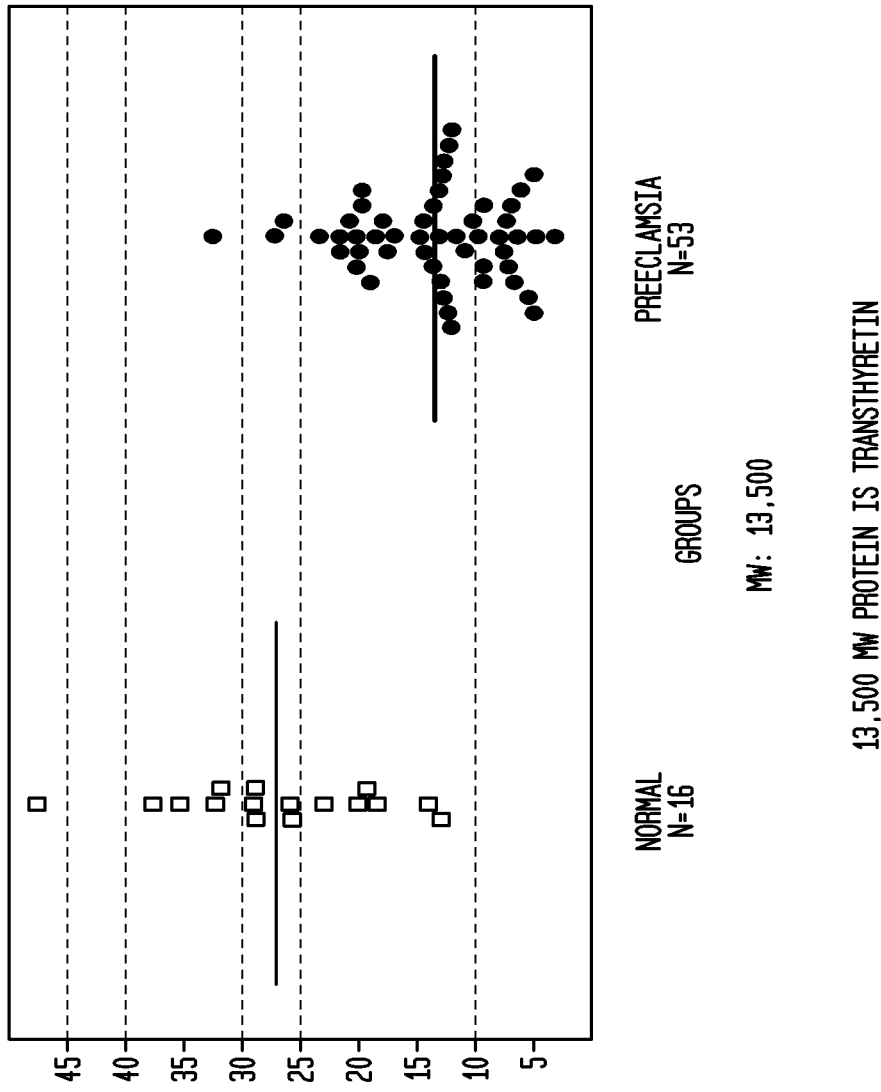
FIG. 1. Shows a proteomic analysis using SELDI-TOF. Human serum from normal pregnancy and preeclamptic pregnancy were subjected to proteomic analysis using SELDI-TOF. The data as shown depicts that a protein of molecular weight of 13,500 is significantly reduced in preeclampsia serum as compared to normal pregnancy serum. Data analyses using suitable protein database suggests that this protein is transthyretin. Horizontal units are treatment groups at the molecular weight (expressed as Daltons) indicated. Vertical units are the relative intensity (RI) of the molecular weight peak in a sample. Different dots represents different patients serum samples (as indicated by N). This figure only shows a abnormal molecular weight region, although the analysis included a range from 3000 to 200,000.

The result of this analysis indicated that number of preeclampsia serum samples (n=53) had a deficiency in a protein having an approximate molecular weight of 14 kDa (FIG. 1).

Example 2

In Vitro Assay for TTR

Figure 2:
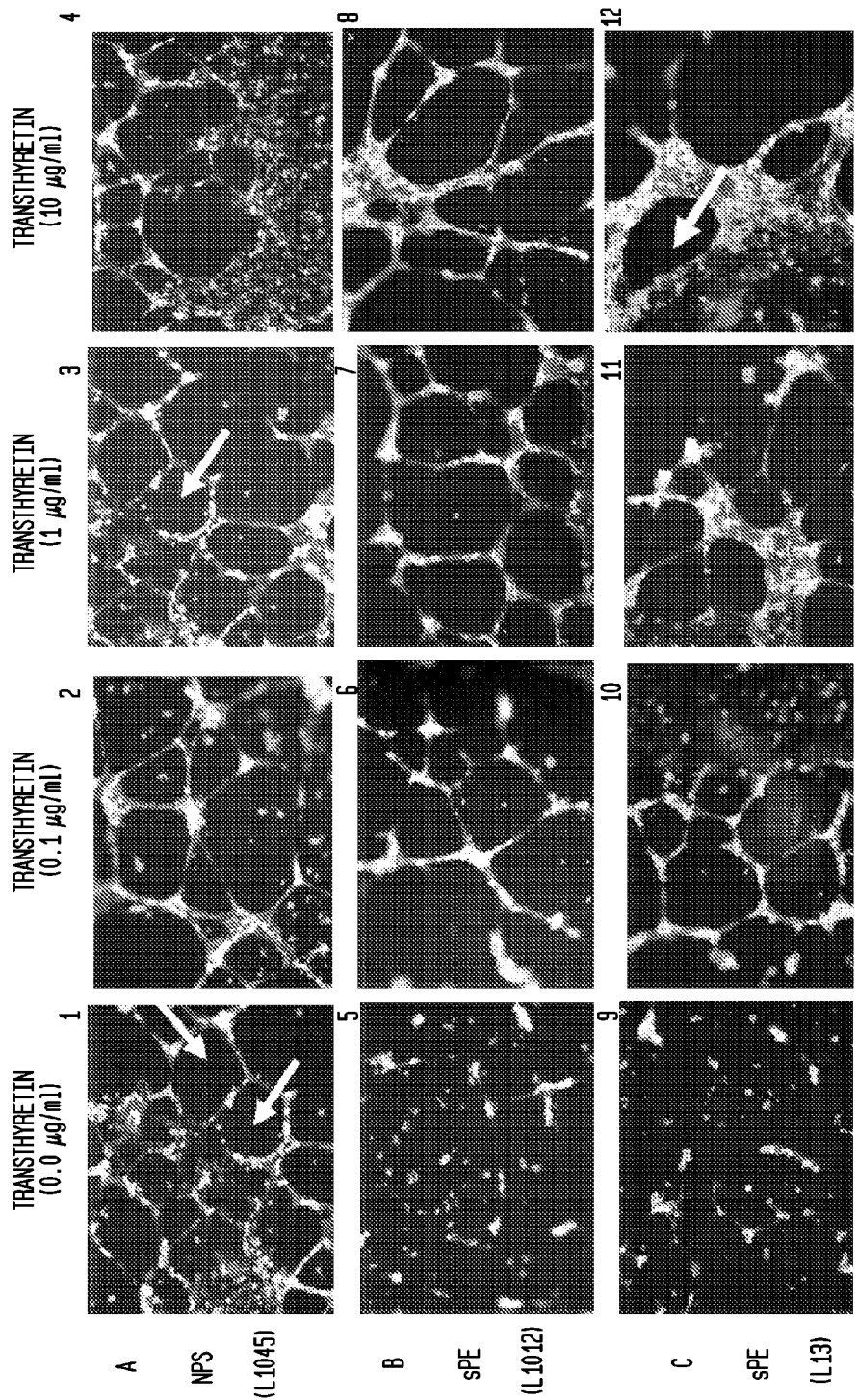
FIG. 2 presents histological data on recombinant transthyretin dose-dependently rescue of severe PE serum induced disrupted EC-HTR8 crosstalk in tube assay. This figure also shows data on severe preeclampsia or sPE (representing samples L1012, L13, L2, L3 L17, L1020).

The in vitro assay described in this example is based on the premise that during normal pregnancy, fetal derived trophoblasts called the "invasive cytotrophoblasts" invade the maternal decidua and the endothelial cell lined spiral arteries. This phenomenon can be restructured using serum from pregnancy as physiological milieu and culturing human umbilical vein endothelial cells and trophoblasts on basement membrane such as matrigel. In response to serum from normal pregnancy, endothelial cells and trophoblasts form a network of tubes as shown in FIG. 2 (Panel A #1). However, serum from pregnancy complications such as preeclampsia disrupts this cross-talk suggesting "disruptive factors" in serum resulting in poor invasion of trophoblasts. For additional information see U.S. Provisional Patent Application No. 61/063,491 filed Feb. 4, 2008 and/or Kalkunte, In Vitro and In Vivo Evidence for Lack of Vascular Remodeling by Third Trimester Trophoblasts, Placenta 29: 871-78 (2008).

Recombinantly produced TTR (detected by SDS-PAGE electrophoresis and purity 96%) was obtained from AbD Serotec, Raleigh, N.C. 27604, USA. Recombinant TTR obtained in lyophilized form was reconstituted with sterile phosphate-saline buffer to obtain a final concentration of 1 mg/ml and maintained at >pH 7.0. The solutions were stored as aliquots frozen at −80° C. until use. Thirty minutes prior to experimentation, the aliquots of TTR were thawed, then mixed with serum and incubated at 37° C. for 30 minutes.

A. Rescue of Severe PE Serum

The in vitro method further includes incubating a co-culture of human endothelial cells and human trophoblast cells in the presence of serum or plasma obtained from a pregnant female for a period of time sufficient to permit vacuolization (also referred to as "capillary formation" and "tube formation" in FIGS. 2-4), and after incubation determining whether substantial vacuolization in the co-culture has occurred by quantification as described in Example 3.

Blood samples were obtained from normal pregnancy human subjects and preeclamptic human subjects during first (6-12 weeks), second (13-20 weeks) or third (21-40 weeks) trimester of pregnancy and serum separated routinely. Pregnancies were considered normal when there were no medical complications. Preeclampsia was defined when blood pressure was >140/90 mm Hg at least on two occasion 4 hours to 1 week apart and with proteinuria>300 milligram in 24 hr urine collection. Preeclampsia can be classified as mild or severe. Severe preeclampsia is characterized by (1) a systolic blood pressure greater than 160 mm Hg or diastolic blood pressure greater than 110 mm Hg on 2 occasions at least 6 hours apart in a woman on bed rest and (2) the presence of significant proteinuria. Marked proteinuria is defined as 5 g or more of protein in a 24-hour urine collection. Severe preeclampsia, at times, may be associated with oligouria, cerebral or visual disturbances, pulmonary edema or cyanosis, epigastric or right upper quadrant abdominal pain, impaired liver function, and thrombocytopenia. In mild preeclampsia (or moderate PE), hypertension and proteinuria are present, but not to these extreme levels, and the patient has no evidence of other organ dysfunction. Exclusion criteria were chronic hypertension, diabetes, antiphospholipid antibody syndrome, thrombophillic anomalies, antepartum and postpartum complications.

During pregnancy, angiogenesis is characterized by spiral artery remodeling for which trophoblast invasion into these maternal blood vessels is a prerequisite. The data of FIG. 2 show an in vitro model of interaction of trophoblasts and endothelial cells that mimics spiral artery remodeling. Specifically, $2.5 \times 10^4$ endothelial cells labeled red and $2.5 \times 10^4$ trophoblasts, labeled green, were co-cultured on matrigel coated plates and stimulated with either NPS (normal pregnancy serum) or severe PES (Preeclampsia Serum) as described above. Exemplary results are shown in FIG. 2. In the absence of exogenous TTR, serum from severe (FIG. 2 Panel B #5 and C #9) preeclampsia patients blocks the "cross-talk" between endothelial-trophoblast cells, causing obvious differences in architecture as compared to the same cells stimulated under the same conditions with NPS serum (sample L1045; FIG. 2 Panel A, #1). Preincubation by mixing of recombinant TTR (AbD Serotec, purity>96%) at different concentrations (0.1, 1.0, 10 microgram/ml of serum) substantially rescues the "abnormal endothelial-trophoblast cross-talk" and is shown in FIG. 2 Panels B & C (#6-8 & 10-12). There was no significant effect on NPS mediated tube formation (FIG. 2, Panel A, #2-4). These cells in these panels exhibit more normal architecture and increases in capillary tube formation.

The number of vacuoles (or tubes) formed per sample were counted. Exemplary results are shown in the graphic panel in FIG. 4. As compared to the control NPS, the cells co-cultured with either mild or severe PE serum exhibited significant decreases in capillary tube formation (60 versus 18 and 14). Statistical significance of experimental differences was assessed using Student's paired t-test. The differences were considered to be statistically significant when the p value was <0.05. As shown in FIG. 4, adding TTR dose dependently increase the number of capillary tubes formed, resulting in the rescue of the abnormal endothelial-trophoblast cross-talk.

B. Rescue of Mild PE Serum

In mild preeclampsia (or moderate PE), hypertension and proteinuria are present, but not to these extreme levels, and the patient has no evidence of other organ dysfunction.

Briefly, $2.5 \times 10^4$ endothelial cells labeled red and $2.5 \times 10^4$ trophoblasts, each from different trimesters labeled green (FIG. 2), were co-cultured on matrigel coated plates and stimulated with either NPS or mild PES as described above. In the absence of exogenous TTR, serum from mild (sample L1033 and L9; FIG. 3 Panel D photograph #13, and Panel E, photograph #17) preeclampsia patients blocks the "cross-talk" between endothelial-trophoblast cells, causing obvious differences in architecture as compared to the same cells stimulated under the same conditions with NPS serum (sample L1045; FIG. 2 Panel A, photograph #1). Preincubation by mixing of recombinant TTR (AbD Serotec, purity>96%) at different concentrations (0.1, 1.0, 10 µg/ml of serum) substantially rescues the "abnormal endothelial-trophoblast cross-talk" and is shown in FIG. 3 Panel D, photograph #14-16 & Panel E, photograph #18-20. The number of vacuoles (or tubes) formed per sample were counted and represented in the graph (FIG. 4, mPE with and without TTR). As compared to the control NPS, the cells co-cultured with mild PE serum exhibited significant decreases in capillary tubes formation (60 versus 20 and 15). Statistical significance of experimental differences was assessed using Student's paired t-test. The differences were considered to be statistically significant when the p value was <0.05.

Example 3

Quantification of Results

The in vitro studies conducted in Example 2 were quantified by counting the number of tube like structures termed as "vacuole" under fluorescence microscope (Nikon Eclipse TS 100 coupled with CCD camera) in four different fields at 4× magnification. Each vacuole in this context is the small cavity completely bound by elongated cellular structure as indicated in FIG. 2 Panel A and FIG. 2 Panel C (shown by bold arrow). As observed under a microscope, vacuolization comprises thin walled vacuoles having few branch points. The branch points are the points from which multiple vacuoles are initiated/connected. The quantity of tubes formed (also means number of vacuoles) will be substantially less by comparison with normal pregnancy serum. Normal pregnancy serum will exhibit tube-vacuole formation over about 50-60 tubes/well of a 48 well plate. These average numbers of such tubes-vacuoles in response to normal pregnancy serum are defined as "normal endothelial-trophoblast cross-talk". In contrast, serum or plasma from a pregnant female at risk for or having preeclampsia will exhibit tube-vacuole formation substantially less under about 50-60 tubes per well. These average numbers of such tubes-vacuoles are defined as "abnormal endothelial-trophoblast cross-talk" (FIG. 4). Dose dependent rescue of "abnormal endothelial-trophoblast cross-talk" by TTR administration is shown in FIG. 4.

Example 4

In Vivo Administration of TTR Rescues Preeclampsia Like Symptoms in a Mouse Model The anti-inflammatory cytokine IL-10 plays a critical role in pregnancy because of its regulatory relationship with other intrauterine modulators and its wide range of immunosuppressive activities. Significantly, its local production by gestational tissues is well documented. We have demonstrated that IL-10 expression by the human placenta was gestational age-dependent, with significant expression through the second trimester followed by attenuation at term. IL-10 expression was also found to be poor in decidual and placental tissues from unexplained spontaneous abortion cases, and from deliveries associated with preterm labor and preeclampsia. However, the mechanism(s) by which IL-10 protects the fetus remains poorly understood; IL-10$^{-/-}$ (knockout) mice suffer no pregnancy defects unless challenged with inflammatory agents. Recently we showed that IL-10$^{-/-}$ mice were more sensitive as compared with wild type counterparts, to "disruptive factors" in PES and exhibit full spectrum of preeclampsia-like symptoms in response to human PES. See U.S. Provisional Patent Application No. 61/063,491 filed Feb. 4, 2008 (PCT Patent Application PCT/US2009/000708). Furthermore, since PE serum is able to disrupt trophoblast and endothelial cell functions, IL-10$^{-/-}$ mice can provide a model system to study the pathogenesis of preeclampsia-like symptoms.

Recombinantly produced TTR (detected by SDS-PAGE electrophoresis and purity 96%) was obtained from AbD Serotec, Raleigh, N.C. 27604, USA. Recombinant TTR obtained in lyophilized form was reconstituted with sterile phosphate-saline buffer to obtain a final concentration of 1 mg/ml and maintained at >pH 7.0. The solutions were stored as aliquots and frozen at −80° C. until use. Thirty minutes prior to experimentation, the aliquots of TTR were thawed, then mixed with 100 µl of PE serum samples. Pregnant IL-10$^{-/-}$ mice (C57BL/6, Jackson Labs, USA) were then injected intraperitoneally on gestational day (g.d.) 10 at a TTR dose of 20 microgram/mouse. The gestational period in mice is 20 days. Similarly, 100 µl PE serum or normal pregnancy serum was administered to different set of animals as control. On g.d.16/17, urine and serum samples were collected from each mouse, and blood pressure measurements were taken. Blood pressure was taken by an established tail-cuff method which utilizes a programmed sphygmomanometer. The animals adapted for 5 min using a warming test chamber (IITC Life Science Inc, Woodland Hills, Calif.) at controlled temperature (35° C.). The measurements were carried out on day 17 of pregnancy using DigiMed blood pressure analyzer, (MicroMed, Louisville, Ky., 40222-4683). Each measurement of blood pressure is an average of three readings at 1 min intervals from a number of animals (~3-5 each). Systolic blood pressure was compared among non-pregnant and pregnant mice. All animals were age matched. Data was analyzed using DigiMed® System Integrator™ Model 400 (DMSI-400).

Total urinary albumen was measures using Albumin (mouse) ELISA kit (ALPCO Diagnostics, Salem, N.H.) and urinary creatinine was measured using Metra Creatinine Kit (Quidel Corporation, San Diego, Calif.). Protinuria as represented as a ration of urinary albumin to creatinine (expressed as µg/mg). (Baseline values seen in mice range from 100-400 µg/mg.)

On g.d. 17 the mice were euthanized, the uterine horns were extracted, photographed and pregnancy outcomes were recorded. The results of the study as summarized in FIG. 5 suggest that a number of PE serum samples representing mild and severe phenotypes induced some or all PE-associated symptoms when injected i.p. on g.d. 10 in IL10$^{-/-}$ mice. The effects in response to only one administration of serum (100 µl) were evaluated on g.d. 17. Signature PE symptoms including intrauterine growth restriction (IUGR) as reflected by reduced fetal weight (representative photographs FIG. 5A and average fetal weights of a number of fetus(n), FIG. 5B), elevated systolic blood pressure (FIG. 5C) and proteinuria (FIG. 5D) were observed in response to PE serum (sPE) when compared to normal pregnancy serum (NPS). Importantly, co-administration of TTR with sPE significantly reversed these PE like symptoms in mice (sPE+TTR group in FIG. 5A-D).

Clinical Example 1

Severe Preeclampsia

A pregnant woman at week 24 of gestation presents herself for routine checkup. Blood pressure measurements show systolic blood pressure is >150 mmHg (hypertension) and urine analysis show excess excretion of protein and creatinine (proteinuria, >1.5). The patient is diagnosed as severe preeclampsia. The subject is treated with a composition of recombinant or isolated human transthyretin protein at a dose of 100 mg/kg body weight over a 24 hour period and the levels of serum transthyretin are monitored by suitable detection method by ELISA or by SELDI-TOF. It is noted that in particular embodiments a dosage of 50-100 mg/kg of recombinant or isolated human transthyretin protein are therapeutic.

Clinical Example 2

Mild Preeclampsia

A pregnant woman at week 28 of gestation presents herself for routine checkup. Blood pressure measurements show systolic blood pressure is >140 mmHg (hypertension) and urine analysis by ELISA show high protein to creatinine ratio (proteinuria) is >0.3, the patient is diagnosed as mild preeclampsia. The subject is treated with a composition of transthyretin protein at a dose of 40 mg/kg body weight over a 24 hour period and the levels of serum transthyretin are monitored by suitable detection method by ELISA or by SELDI-TOF. The clinical outcome of hypertension and proteinuria are monitored during the following week. Depending on the clinical diagnosis, a second dose of 40 mg/kg is given over a 24 hr period. It is noted that in particular embodiments a dosage of 25-50 mg/kg of recombinant or isolated human transthyretin protein are therapeutic.

Clinical Example 3

Severe Preeclampsia

A pregnant woman at week 22 of gestation presents herself for routine checkup. Blood pressure measurements show systolic blood pressure is >155 mmHg (hypertension) and urine analysis show excess excretion of protein and creatinine (proteinuria, >1.5), the patient is diagnosed as severe preeclampsia. The subject is treated with a composition of transthyretin protein in combination with diclofenac 10:1 (mole/mole) at a dose of 10 mg/kg per day administered over a 24 hour period and the levels of serum transthyretin is monitored by suitable detection method by ELISA or by SELDI-TOF. The clinical outcome of hypertension and proteinuria are monitored in the following week. Depending on the outcomes, a second dose of 5-10 mg/kg of transthyretin-diclofenac is administered over a 24 hr period.

It is noted that in particular embodiments the mole ratio of transthyretin protein to diclofenac is from about 1:1 to about 10:1. It is further noted that an initial dosage of about 5-100 mg/kg/day is contemplated (total transthyretin protein plus NSAID). Without being bound by any particular theory it is believed that NSAIDs such as diclofenac act to stabilize transthyretin protein in vivo. Note is further made of NSAIDs such as Ibuprofen, Naproxen, Fenoprofen, Ketoprofen, Flurbiprofen, Oxaprozin, Indomethacin, Sulindac, Etodolac, Piroxicam, Meloxicam, Tenoxicam, Droxicam, Lornoxicam, Isoxicam, Mefenamic acid, Meclofenamic acid, Flufenamic acid, Tolfenamic acid, Celecoxib, Rofecoxib Valdecoxib, Parecoxib Lumiracoxib and Etoricoxib Clinical Example 4

Severe Preeclampsia

Functional Peptides/Fragments

A pregnant woman at week 26 of gestation presents herself for routine checkup. Blood pressure measurements show systolic blood pressure is >155 mmHg (hypertension) and urine analysis show excess excretion of protein and creatinine (proteinuria, >1.5). The patient is diagnosed as severe preeclampsia. The subject is treated with a composition consisting of functional peptides/fragments of synthetic transthyretin protein at a dose of 50-100 mg; preferably 20 mg/kg per day over a 24 hour period, Subsequent to dosing, the patient's levels of serum transthyretin are monitored by suitable detection method by ELISA or by SELDI-TOF. The clinical outcome of hypertension and proteinuria are monitored in the following week. Depending on the outcomes, a second dose of 10-20 mg/kg of said transthyretin composition is given over a 24 hour period. Included in said composition are synthetic transthyretin as exemplified by

```
                                            (SEQ ID NO: 1)
H-PTGTGESKAPLMVKVLDAVRGSPAINVAVHVFRKAADDTW

EPFASGKTSE (SEQ ID NO: 2)
-NH-CH2-CH2-S-CH2-CO-ELHGLTTEEEFVEGIYKVEIDT

KSYWKALGISPFHEHAEVVFTAND (SEQ ID NO: 3)
-NH-CH2-CH2-S-CH2-CO-PRRYTIAALLSPYSYSTTAVV

TNPKE-OH
``` or their fragment peptides exemplified by

```
                                            (SEQ ID NO: 2)
Cl-Ac-ELHGLTTEEEFVEGIYKVEIDTKSYWK[[-]]ALGI

SPFHEHAEVVFTAND (SEQ ID NO: 3)
-NH-CH2-CH2-S-CH2-CO-PRRYTIAALLSPYSYSTTAVV

TNPKE-OH
``` or other non-limiting peptide fragments indicated in the reference "Synthesis of an analog of the thyroid hormone-binding protein transthyretin via regioselective chemical ligation." Wilce J A, Love S G, Richardson S J, Alewood P F, Craik D J. J Biol Chem, 2001 Jul. 13; 276(28):25997-6003). The composition indicated is also contemplated to include biologically active agent fusions of transthyretin such as PEG-TTR (PEG-TTR variant) (incorporated in its entirety US patent application 20090191624 Use of transthyretin peptide/protein fusions to increase the serum half-life of pharmacologically active peptides/proteins).

Clinical Example 5

Severe Preeclampsia/HELLP

A pregnant woman at week 24 of gestation presents herself for routine checkup. Blood pressure measurements show systolic blood pressure of 170 mmHg (hypertension) and urine analysis show excess excretion of protein and creatinine (proteinuria, 7.0), the patient is initially diagnosed as severe preeclampsia. Additionally, the blood analysis for liver function test show elevated levels of liver enzymes AST and ALT and elevation in platelet count. The patient now is confirmed with a diagnosis of HELLP syndrome. The subject is treated with a composition consisting of transthyretin protein in combination with aspirin 10:1 mole ratio at dose of 50-100 mg, preferably at 20 mg/kg per day over a 24 hour period and the levels of serum transthyretin and platelet count is monitored by suitable detection method. The clinical outcome of hypertension and proteinuria are monitored in the following week. Depending on the outcomes, a second dose of 10-20 mg/kg of said transthyretin composition is given over a 24 hr period.

Clinical Example 6

Severe Preeclampsia

A pregnant woman at week 27 of gestation presents herself for routine checkup. Blood pressure measurements show systolic blood pressure of 160 mmHg (hypertension) and urine analysis show excess excretion of protein and creatinine (proteinuria, 5.0), the patient is initially diagnosed as experiencing severe preeclampsia. Additionally, the blood analysis for liver function test show elevated levels of liver enzymes AST and ALT and elevation in platelet count. The patient now has a confirmed diagnosis of HELLP syndrome. The subject is treated with a composition consisting of transthyretin protein stabilized with aspirin (5:1 mole ratio) at a dose of 50-100 mg, preferably 20 mg/kg per day over a 24 hour period and the levels of serum transthyretin and platelet count are monitored by suitable detection method. The clinical outcome of hypertension and proteinuria are monitored in the following week. Depending on the outcomes, a second dose of 10-20 mg/kg of said transthyretin composition is given over a 24 hr period.

Contemplated therapeutic compositions for this example are further to comprise hepatoprotectant (e.g., silymarin, flavobion, thioctacid) and anti-oxidants such as vitamin C, lipoic acid and minerals and vitamins including but not limited to Vitamin B12, Vitamin B3.

Clinical Example 7

Severe Preeclampsia

A pregnant woman at week 24 of gestation presents herself for routine checkup. Blood pressure measurements show systolic blood pressure is >160 mmHg (hypertension) and urine analysis show excess excretion of protein and creatinine (proteinuria, >4.5), the patient is diagnosed as severe preeclampsia. The patient is treated with a composition of transthyretin mutant proteins exemplified by mutation in serine residue Ser$^{117}$→Cys (S117C)], glutamine acid residue Glu$^{92}$→Cys (E92C) or threonine residue [(T119→Methionine (T119M)] with or without further stabilizations at a dose of 50-100 mg/kg body weight over a 24 hour period and the levels of serum transthyretin are monitored by suitable detection method by ELISA or by SELDI-TOF. The serum samples after treatment are also monitored for their ability to support the endovascular dual cells tube formation and compared with the disruptive activity of the serum samples before treatment. A methodology of using an in vitro approach is presented in detail in the PCT patent application WO/2009/099603.

Clinical Example 8

Eclampsia

A pregnant woman at week 28 of gestation presents has progressed from preeclampsia to eclampsia exhibiting tonic-clonic seizures. Blood pressure measurements show systolic blood pressure is >150 mmHg (hypertension) and urine analysis show excess excretion of protein and creatinine (proteinuria, >1.5). The patient is diagnosed as eclampsia. The subject is treated with a composition of recombinant or isolated human transthyretin protein at a dose of 100 mg/kg body weight over a 24 hour period and the levels of serum transthyretin are monitored by suitable detection method by ELISA or by SELDI-TOF.

The pharmacologically active compositions of this invention can be processed in accordance with conventional methods of Galenic pharmacy to produce medicinal agents for administration to subjects, e.g., mammals including humans.

The compositions of this invention individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules, vials, and injector cartridges are convenient unit dosages.

Also for parenteral application, particularly suitable are tablets, dragees, liquids, drops, suppositories, or capsules. A syrup, elixir, or the like can be used wherein a sweetened vehicle is employed. Sublingual and buccal forms are also noted.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising 3.5-500 mg of TTR or active fragments or TTR mutations. And in particular embodiments this is combined with NSAIDs in a ration of about 10:1 to about 1:1 (molar) in a pharmaceutically acceptable carrier per unit dosage.

All patents, patent applications, publications, and other references cited herein are hereby incorporated by reference in their entirety. Although the invention has been particularly described with reference to certain preferred embodiments, artisans of ordinary skill will appreciate that changes in form and details may be made without departing from the scope of the appended claims.

REFERENCES

1. DiFederico et al., Preeclampsia is associated with widespread apoptosis of placental Cytotrophoblasts within the uterine wall, Am J Pathol 155:293-301 (1999).
2. Genebacev et al., Invasive cytotrophoblast apoptosis in preeclampsia. Hum Reprod 14 (suppl 2):59-66 (1999).
3. Leung et al., Increased placental apoptosis in pregnancies complicated by preeclampsia, Am J Obstet Gynecol 184: 1249-50 (2001).
4. Balkundi et al., Labor-associated changes in Fas ligand expression and function in human placenta. Pediatr Res 47:301-08 (2000).
5. Venkatesha et al., S9oluble endoglin contributes to the pathogenesis of preeclampsia. Nat Med 12(6):642-49 (2006).
6. Peracoli et al., Tumor necrosis factor-alpha in gestation and puerperium of women with gestational hypertension and preeclampsia, Am J Reprod Immunol 57(3):177-85 (2007).
7. Jonsson et al., Cytokine mapping of sera from women with preeclampsia and normal 0pregnancies, J Reprod Immunol 70(1-2):83-91 (2006).
8. Banerjee et al., Placental expression of interferon-gamma (IFN-γ) and its receptor IFN-γ R2 fail to switch from early hypoxic to late normotensive development in preeclampsia, J Clin Endocrinol Metab 90(2):944-52 (2005).
9. Hendler et al., The levels of leptin, adiponectin, and resistein in normal weight, overweight, and obese pregnant women with and without preeclampsia, Am J Obstet Gynecol 193(3 Pt2):979-83 (2005).
10. Shah, D. M., Role of the renin-angiotensin system in the pathogenesis of preeclampsia, Am J Physiol Renal Physiol 288(4):F614-25 (2005).
11. Salmon et al., Antiphospholipid antibodies and pregnancy loss: A disorder of inflammation, J Reprod Immunol 2008, vol. 77, no 1, pp. 51-56
12. Girardi et al., Heparin prevents antiphospholipid antibody-induced fetal loss by inhibiting complement activation, Nat Med 10(11):1222-26 (2004).
13. Sharma et al., Leptin, IL-10 and inflammatory markers (TNF-γ, IL-6 and IL-8) in pre-eclamptic, normotensive pregnant and healthy non-pregnant women, Am J Reprod Immunol 58(1):21-30 (2007).
14. U.S. Pat. Nos. 6,735,529; 6,620,590; 6,495,330 and 6,258,540 and United States Patent Publication Nos. 2007/0185200; 2004/0038305; 2007/0178530; 2007/0104707; 2007/0020766; 2006/0183175 and 2005/0074746.
15. PCT Patent Publication WO2008/046160 (PCT Application No. AU2007/001598 filed 19 Oct. 2007 and entitled Assay for the Detection of Biomarkers Associated with Pregnancy Related Conditions); Vascotto et al., Oxidized transthyretin in amniotic fluid as an early marker of preeclampsia, J Proteome Res: 2007, 6 (1), pp 160-170; and Atkinson, K. R. L., Proteomic Biomarker Discovery for Preeclampsia, Doctor of Philosophy in Biological Sciences thesis, The University of Auckland, 2008 (which discloses that upregulation of transthyretin may indicate its utility as a preeclampsia biomarker). (Page 147)
16. U.S. Pat. No. 4,816,388 filed 30 Oct. 1985 entitled Human Prealbumin and Related Methods and Products.
17. Duan et al., Isolation, characterization, cDNA cloning and gene expression of an avian transthyretin, Eur J Biochem 200:679-87 (1991) and various other publications cited in the latter (references 3, 4, and 20-28).
18. Buxbaum et al., Transthyretin protects Alzheimer's mice form the behavioral and biochemical effects of Aβ toxicity, Proc Natl Acad Sci 105:2681-86 (2008).
19. Stein et al., Neutralization of transthyretin reverses the neuroprotective effects of secreted amyloid precursor protein (APP) in APP$_{Sw}$ mice resulting in tau phosphorylation and loss of hippocampal neurons: support for the amyloid hypothesis, J Neurosci 24(35):7707-17 (2004).
20. PCT Patent Publication WO 2006/071469 filed 2 Dec. 2004 entitled Modulation of the Neuroendocrine System as a Therapy for Motor Neuron Disease.
21. Myers et al., Use of proteomic patterns as a novel screening tool in preeclampsia, J Obstet Gynaecol. 24(8): 873-4 (2008). Park et al., Identification of proteomic biomarkers of preeclampsia in amniotic fluid using SELDI-TOF mass spectrometry. Reprod Sci. 15(5):457-68 (2008).

The invention claimed is:

1. A method of treating a pre-eclampsia (PE)-type disorder in a subject in need of such treatment comprising administering to the subject a pharmaceutical composition containing a therapeutically effective amount of a transthyretin (TTR) polypeptide in admixture with a pharmaceutically acceptable vehicle wherein said TTR polypeptide is selected from the group consisting of TTR (Uniprot: P02766), TTR fragment Ser[137] to Cys, glutamic acid residue Glu[122] to Cys, threonine residue T[139] to Methionine, or a TTR fragment selected from the group consisting of SEQ ID NOs:1, 2, and 3.

2. The method according to claim 1 wherein the preeclampsia-type disorder is preeclampsia.

3. The method according to claim 1 wherein the preeclampsia-type disorder is eclampsia.

4. The method according to claim 1 wherein the preeclampsia-type disorder is HELLP syndrome.

5. The method according to claim 1 wherein said TTR polypeptide comprises TTR.

6. The method according to claim 1 wherein said TTR polypeptide comprises a polypeptide selected from the group consisting of

```
                                                 (SEQ ID NO: 1)
H-PTGTGESKAPLMVKVLDAVRGSPAINVAVHVFRKAADDTW
EPFASGKTSE,
                                                 (SEQ ID NO: 2)
-NH-CH2-CH2-S-CH2-CO-ELHGLTTEEEFVEGIYKVEIDT
KSYWKALGISPFHEHAEVVFTAND,
                                                 (SEQ ID NO: 3)
-NH-CH2-CH2-S-CH2-CO-PRRYTIAALLSPYSYSTTAVVT
NPKE-OH.
```

7. The method according to claim 1 wherein said therapeutically effective amount of TTR polypeptide is between about 50 and 500 micrograms per kilogram body weight.

8. The method of claim 1 wherein said therapeutically effective amount of TTR polypeptide is about 25-100 mg/kg.

9. The method of claim 8 wherein said therapeutically effective amount of TTR polypeptide is about 25-50 mg/kg.

10. The method of claim 1 wherein said therapeutically effective amount of TTR polypeptide is administered over a 24 hour period.

11. The method according to claim 1 wherein said TTR polypeptide is co-administered with a non-steroidal anti-inflammatory (NSAID).

12. The method according to claim 11 wherein said TTR polypeptide is co-administered with said NSAID at a molar ratio of TTR polypeptide to NSAID of from about 10:1 to about 1:1.

13. The method according to claim 1 wherein said TTR polypeptide is a stabilized TTR complex.

14. The method according to claim 13 wherein said TTR-complex includes stable TTR complexes with NSAIDS, metal cations, small molecular weight compounds including aromatic, heterocyclic, phenolics, arylheterocyclic and their derivatives, amino acids.

15. The method according to claim 11 wherein the non-steroidal anti-inflammatory composition is selected from the group consisting of diclofenac, flufenamic acid, diflunisal and aspirin.

16. The method of claim 11 wherein said co-administered amount of a TTR polypeptide and NSAID comprises from about 5 to about 100 mg/kg/day.

17. The method of claim 1 further comprising the step of monitoring the level of serum transthyretin in said subject subsequent to said administration.

18. The method according to claim 1 wherein the disorder is a hypertensive disorder.

19. The method according to claim 1 wherein the disorder is a kidney pathology, glomerular endotheliosis and excess excretion of protein or proteinuric disorders.

20. The method according to claim 1 wherein the disorder is of placental origin.

21. The method according to claim 1 wherein said treatment is maintained at a level that induces pro-angiogenesis.

22. The method according to claim 1 wherein said treatment prevents the restriction of intrauterine growth.

23. The method according to claim 1 wherein said TTR polypeptide comprises a polypeptide selected from the group consisting of

```
                                                 (SEQ ID NO: 1)
H-PTGTGESKAPLMVKVLDAVRGSPAINVAVHVFRKAADDTWEPFASGKT
SE,
or
                                                 (SEQ ID NO: 3)
NH-CH2-CH2-S-CH2-CO-PRRYTIAALLSPYSYSTTAVVTNPKE-OH.
```

* * * * *